United States Patent
Bongers

(10) Patent No.: US 10,650,299 B2
(45) Date of Patent: May 12, 2020

(54) WEARABLE DEVICE AND SYSTEM

(71) Applicant: KONINKLIJKE PHILIPS N.V., Eindhoven (NL)

(72) Inventor: Edwin Gerardus Johannus Maria Bongers, Thorn (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/082,299

(22) PCT Filed: Mar. 22, 2017

(86) PCT No.: PCT/EP2017/056882
§ 371 (c)(1),
(2) Date: Sep. 5, 2018

(87) PCT Pub. No.: WO2017/162776
PCT Pub. Date: Sep. 28, 2017

(65) Prior Publication Data
US 2019/0042905 A1    Feb. 7, 2019

(30) Foreign Application Priority Data

Mar. 22, 2016 (EP) .................................. 16161720

(51) Int. Cl.
G06K 19/077    (2006.01)
G06K 19/00     (2006.01)
(Continued)

(52) U.S. Cl.
CPC ..... G06K 19/07762 (2013.01); G06K 7/0008 (2013.01); G06K 19/00 (2013.01);
(Continued)

(58) Field of Classification Search
CPC ......... H04L 63/10; H04L 63/18; H04L 67/12; H04Q 2209/40
See application file for complete search history.

(56) References Cited

U.S. PATENT DOCUMENTS

2004/0131897 A1* 7/2004 Jenson ................ H01M 2/0267
429/7
2010/0001855 A1* 1/2010 Amir .................... G06K 7/0008
340/539.3
(Continued)

FOREIGN PATENT DOCUMENTS

CN    104536314    4/2015
CN    204596099    8/2015
(Continued)

OTHER PUBLICATIONS

MarketsandMarkets, Wearable Electronics Market and Technology Analysis (2013-2018).
(Continued)

*Primary Examiner* — Fabricio R Murillo Garcia

(57) ABSTRACT

The present invention relates to a wearable device and a system. The wearable device (20, 40) comprises an electronic circuit (21), a power supply (22), a switching circuit (23, 43) coupled between the electronic circuit and the power supply, and an electromagnetic field detection circuit (24) coupled to the switching circuit (23, 43) for detecting an electromagnetic field generated by an NFC transmitter within the detection range of the electromagnetic field detection circuit and for generating a trigger signal if an electromagnetic field generated by an NFC transmitter is detected within the detection range of the electromagnetic field detection circuit. The switching circuit (23, 43) comprises a flip-flop (231) or a transistor circuit (431) including an input transistor (432) and a fuse (433) to switch the connection between the electronic circuit and the power supply on in response to the trigger signal.

13 Claims, 2 Drawing Sheets

LEGEND
1: SYSTEM
10: NFC TRANSMITTER
11: PORTABLE DEVICE
12: NFC CIRCUITRY
13: TRANSMITTER ANTENNA
20: WEARABLE DEVICE
21: ELECTRONIC CIRCUIT
22: POWER SUPPLY
23: SWITCHING CIRCUIT
24: ELECTROMAGNETIC FIELD DETECTION CIRCUIT
25: CONNECTION LINE
26: FEEDING LINE
27: GATE LINE
28: CONNECTION
29: CASING
30: DATA
31: ENERGY
32: NFC
231: FLIP-FLOP
232: SWITCHING TRANSISTOR
233: GATE
234: SOURCE
235: DRAIN
241: DEVICE ANTENNA
242: NFC TAG

(51) Int. Cl.
  *G16H 10/00* (2018.01)
  *G06K 7/00* (2006.01)
  *G06Q 20/32* (2012.01)
  *H01M 2/02* (2006.01)
  *H04B 5/00* (2006.01)
  *G16H 10/65* (2018.01)
  *G16H 40/63* (2018.01)

(52) U.S. Cl.
  CPC ............ *G16H 10/00* (2018.01); *G16H 10/65* (2018.01); *G16H 40/63* (2018.01); *G06Q 20/3278* (2013.01); *H01M 2/0267* (2013.01); *H04B 5/0031* (2013.01)

(56) References Cited

U.S. PATENT DOCUMENTS

2010/0176202 A1   7/2010   Teraoka et al.
2010/0248710 A1   9/2010   Sklovsky
2014/0120832 A1*  5/2014   Confer ................ H04B 5/0031
                                                       455/41.1

FOREIGN PATENT DOCUMENTS

EP      2843847       3/2015
FR      2898201       9/2007
WO      2006/114297   11/2006

OTHER PUBLICATIONS

Robert Triggs, "What is NFC & how does it work?" http://www.androidauthority.com/what-is-nfc-270730.

NXP Semiconductors, "NFC Forum Type 2 Tag compliant IC with 144/888 bytes user memory and field detection" NTAG213F/216F, Sep. 28, 2015 http://www.nxp.com/documents/data_sheet/NTAG213F_216F.pdf.

* cited by examiner

LEGEND

| | | | |
|---|---|---|---|
| 1: | SYSTEM | 30: | DATA |
| 10: | NFC TRANSMITTER | 31: | ENERGY |
| 11: | PORTABLE DEVICE | 32: | NFC |
| 12: | NFC CIRCUITRY | 231: | FLIP-FLOP |
| 13: | TRANSMITTER ANTENNA | 232: | SWITCHING TRANSISTOR |
| 20: | WEARABLE DEVICE | 233: | GATE |
| 21: | ELECTRONIC CIRCUIT | 234: | SOURCE |
| 22: | POWER SUPPLY | 235: | DRAIN |
| 23: | SWITCHING CIRCUIT | 241: | DEVICE ANTENNA |
| 24: | ELECTROMAGNETIC FIELD DETECTION CIRCUIT | 242: | NFC TAG |
| 25: | CONNECTION LINE | | |
| 26: | FEEDING LINE | | |
| 27: | GATE LINE | | |
| 28: | CONNECTION | | |
| 29: | CASING | | |

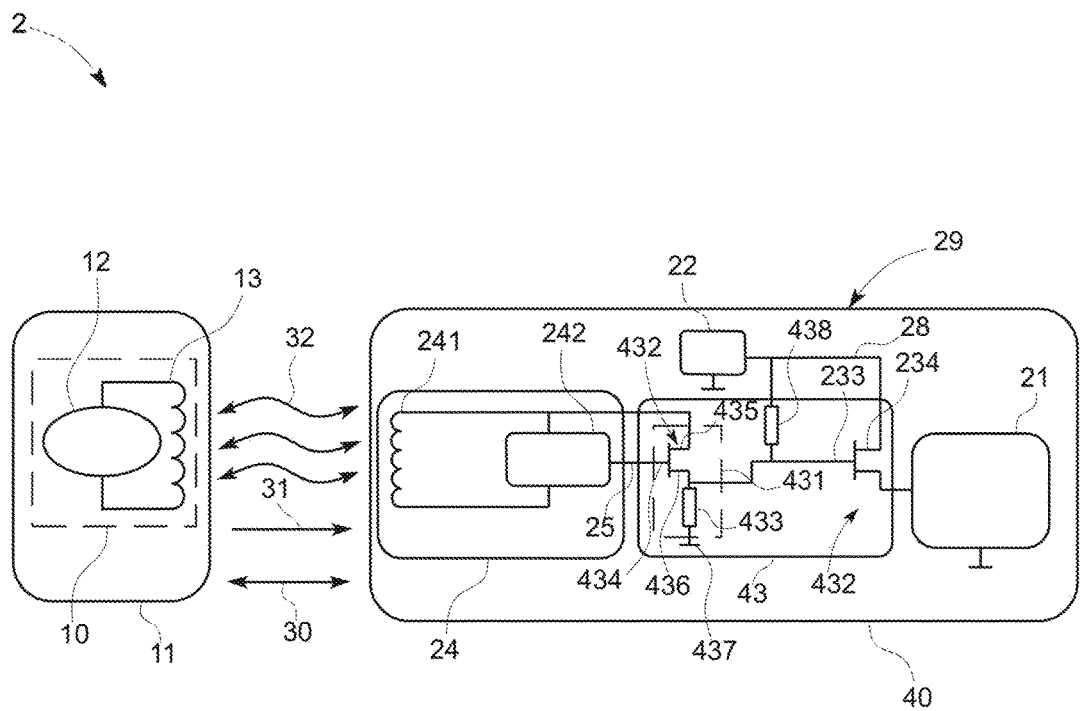

FIG. 2

LEGEND

| | | | |
|---|---|---|---|
| 2: | SYSTEM | 30: | DATA |
| 10: | NFC TRANSMITTER | 31: | ENERGY |
| 11: | PORTABLE DEVICE | 32: | NFC |
| 12: | NFC CIRCUITRY | 233: | GATE |
| 13: | TRANSMITTER ANTENNA | 234: | SOURCE |
| 20: | WEARABLE DEVICE | 235: | DRAIN |
| 21: | ELECTRONIC CIRCUIT | 241: | DEVICE ANTENNA |
| 22: | POWER SUPPLY | 242: | NFC TAG |
| 23: | SWITCHING CIRCUIT | 431: | TRANSISTOR CIRCUIT |
| 24: | ELECTROMAGNETIC FIELD DETECTION CIRCUIT | 432: | INPUT TRANSISTOR |
| 25: | CONNECTION LINE | 433: | FUSE |
| 26: | FEEDING LINE | 434: | GATE |
| 27: | GATE LINE | 435: | SOURCE |
| 28: | CONNECTION | 436: | DRAIN |
| 29: | CASING | 437: | GROUND |
| | | 438: | RESISTOR |

WEARABLE DEVICE AND SYSTEM

CROSS REFERENCE TO RELATED APPLICATIONS

This application is the U.S. National Phase application under 35 U.S.C. § 371 of International Application No. PCT/EP2017/056882, filed Mar. 22, 2017, published as WO 2017/162776 on Sep. 28, 2017, which claims the benefit of European Patent Application Number 16161720.4 filed Mar. 22, 2016. These applications are hereby incorporated by reference herein.

FIELD OF THE INVENTION

The present invention relates to a wearable device and a system.

BACKGROUND OF THE INVENTION

Today, several types of wearable device exist, with development of various types of wearable technologies and advancements in wearable computing. The term 'wearable device' refers to any electronic device or product which can be worn by a subject, e.g. a person, to integrate computing in his daily activity or work and use technology to avail advanced features & characteristics.

Typically, any wearable device may include one or more of the following elements including sensors, actuators, image and/or speech recognition technologies, positioning and/or networking chips, displays and/or optoelectronics and specialty monitoring devices. The emphasis on using wearable devices for fitness, health monitoring, entertainment, enterprise and industrial applications has been increasing with advancements such as stretchable electronics, flexible circuits, conducting fabrics, long lasting batteries and smaller specialty wearable sensors.

Remote monitoring and wearable technologies could also help to effectively manage health, monitor safety and reduce the staggering health care costs. For instance, health patches including means for measuring vital signs or any signals from the subject are currently in development for use in the hospital and at home.

As long lasting patches are very important, battery management becomes more and more relevant. To power up patches, switches can be used to activate the patch just before operation. This will safe battery power and increase life time. Besides the life time, costs will also play an important role, since the patches are (semi-)disposable. Additionally, switches will involve extra costs which is not desired in disposables.

Once solution to the problem of how to switch on the patch is the use of a zinc-air battery. The patch is enclosed in a sealed package and so the battery is deactivated. Once the package is opened by the user a chemical process inside the battery will start immediately and power is available. This results in powering up the system and the patch is ready to work. However, problems with bad sealed packages have been experienced. Due to pre-discharge of the battery the patch will not work once the user (e.g. a caregiver or nurse) wants to place the patch onto the patient. Another issue is the patch-patient pairing. For this purpose a Bluetooth smart radio may be placed on board of the patch, and with an application program e.g. on a tablet or smartphone pairing has to be done. Having multiple unassigned Bluetooth devices on air can, however, result in wrong patch-patient paring which will have serious consequences.

US2004/0131897 discloses an active wireless tagging system for a flexible peel-and-stick battery-operated device. The device comprises an RFID tag for communication with a remote RF interrogator. An RF-activated switch serves to connect the thin-film battery to the electronic circuit of the tag. RF energy received by the antenna is detected and amplified. A switch is closed operatively coupling battery power to the electronics circuit.

SUMMARY OF THE INVENTION

It is an object of the present invention to provide a wearable device and a system which solve the problem of how to switch on the wearable device in an easy, inexpensive and reliable manner. It is a further object of the present invention to provide a wearable device and a system which solve the problem of how to solve the patch-patient pairing problem.

In a first aspect of the present invention a wearable device is presented comprising:
an electronic circuit,
a power supply,
a switching circuit coupled between the electronic circuit and the power supply, and
an electromagnetic field detection circuit coupled to the switching circuit for detecting an electromagnetic field generated by an NFC transmitter within the detection range of the electromagnetic field detection circuit and for generating a trigger signal if an electromagnetic field generated by an NFC transmitter is detected within the detection range of the electromagnetic field detection circuit,
wherein said switching circuit comprises a flip-flop or said switching circuit includes a transistor circuit including an input transistor and a fuse to switch the connection between the electronic circuit and the power supply on in response to the trigger signal,
wherein the fuse is configured to melt in response to detection of the electromagnetic field generated by the NFC transmitter to allow the input transistor to switch the connection between the electronic circuit and the power supply on in response to the trigger signal.

In a further aspect of the present invention a system is presented comprising
a wearable device as disclosed herein and
an NFC transmitter for generating an electromagnetic field for detection by the wearable device to activate the wearable device.

Preferred embodiments of the invention are defined in the dependent claims. It shall be understood that the claimed system has similar and/or identical preferred embodiments as the claimed device, in particular as defined in the dependent claims and as disclosed herein.

The present invention is based on the idea to use Near Field Communication (NFC) for activating the wearable device (in particular a patch) and for device-patient pairing. NFC enables short range communication between compatible devices. From a device perspective the NFC communication and pairing goes passively. The idea is to use the energy transmitted by an NFC transmitter (e.g. a separate device or implemented by use of an existing electronic device, such as a smartphone or tablet) and an NFC tag included in the wearable device to trigger an electronic switch to power up the wearable device, in particular an electronic circuit included in the wearable device, e.g. sensor or measurement circuitry to measure a vital sign. Hence, the wearable device does not need to be in a deep sleep or standby mode (which consumes power), but can completely switched on passively. In this way the costs and surface of a physical switch, as provided in known wearable devices, can be saved and the wearable device has a maximum shelf time, which is only determined by the self-discharge of the power supply (e.g. a battery) of the wearable device.

In an embodiment the switching circuit comprises a switching transistor, which is a cost-effective and simple solution that does not require much power to be controlled. Hereby, in a practical implementation the gate of the switching transistor is connected to the output of the flip-flop or the transistor circuit, the source of the switching transistor is connected to the power supply and the drain of the switching transistor is connected to the electronic circuit.

In a preferred embodiment the switching circuit comprises the flip-flop and is configured to switch the connection between the electronic circuit and the power supply on or off in response to the trigger signal. A flip-flop can be easily and cheaply realized without requiring much space.

In an alternative embodiment the switching circuit comprises the transistor circuit including an input transistor and a fuse and is configured to switch the connection between the electronic circuit and the power supply permanently on in response to the trigger signal. Hereby, a flip-flop has a smaller foot print since building a flip-flop with separate transistors requires more space compared to an integrated flip-flop.

In a practical implementation the switching circuit comprises the transistor circuit including an input transistor and a fuse and the gate and the source of the input transistor are connected to the electromagnetic field detection circuit. Further, the fuse is preferably coupled between the drain of the input transistor and ground and is configured to melt in response to detection of the electromagnetic field generated by the NFC transmitter. Hence, by melting the fuse a one-time activation can be achieved, i.e. the wearable sensor can not be deactivated afterwards, contrary to the embodiment using the flip-flop which can be activated and deactivated again and again.

The gate of the switching transistor is preferably also connected to the terminal of the fuse, which is connected to the drain of the input transistor and/or a resistor is coupled between the power supply and the gate of the switching transistor. This provides for a simple and inexpensive, but reliable solution.

The fuse may be a low power fuse and/or the resistor may be a pull up mega-ohm resistor.

In a further embodiment the electromagnetic field detection circuit is configured to generate a trigger signal in response to reception of an identifier identifying the device and/or the NFC transmitter and/or a command from the NFC transmitter. In an implementation the coding of the wearable device, e.g. an NFC tag included therein as part of the electromagnetic field detection circuit, to provide a reliable and safe pairing of the wearable device to the patient, i.e. wrong patch-patient pairing can be reliably avoided.

Preferably, the electromagnetic field detection circuit comprises an NFC tag and an antenna or coil. Such components can be cheaply manufactured and thus be used in disposable products.

In another embodiment the device further comprises a watertight and/or airtight cover, which is easily possible due to the lack of a physical switch.

The present invention may be applied in various practical scenarios where a wearable device shall be reliably and easily activated. In one practical application the wearable device is a medical wearable device, in particular a patch for mounting at a subject, and wherein the NFC transmitter is configured as or included in a portable device, in particular a smartphone or tablet.

BRIEF DESCRIPTION OF THE DRAWINGS

These and other aspects of the invention will be apparent from and elucidated with reference to the embodiment(s) described hereinafter. In the following drawings FIG. 1 shows a schematic diagram of a first embodiment of a system and wearable device according to the present invention and FIG. 2 shows a schematic diagram of a second embodiment of a system and wearable device according to the present invention.

DETAILED DESCRIPTION OF THE INVENTION

Figure 1:
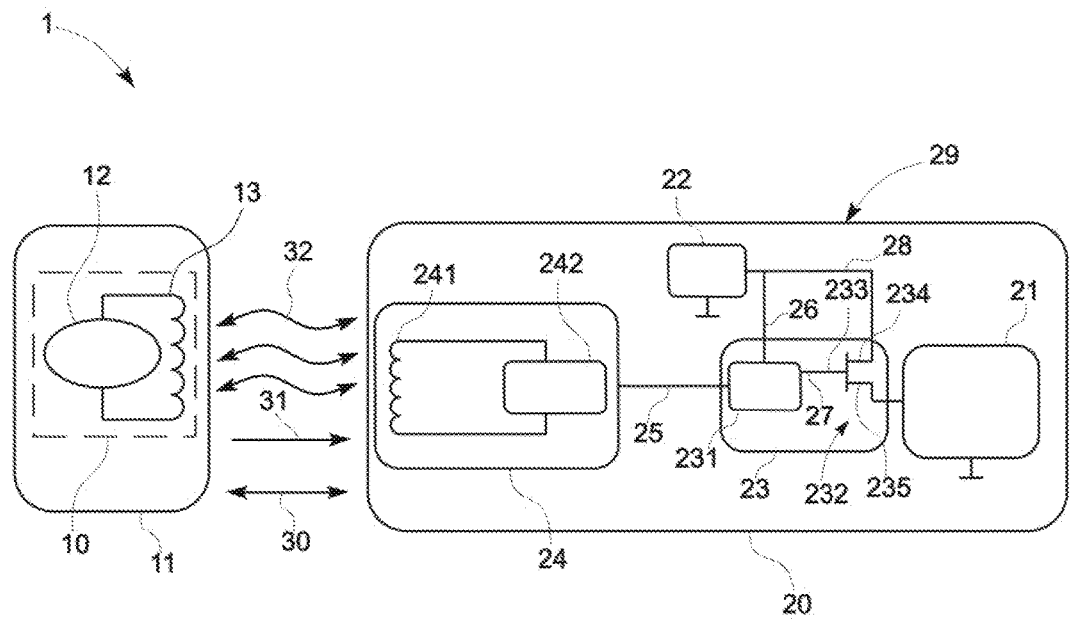

FIG. 1 shows a schematic diagram of a first embodiment of a system 1 and wearable device 20 according to the present invention. The system 1 comprises an NFC transmitter 10 and a wearable device 20 (or several wearable devices). The NFC transmitter 10 is configured to generate an electromagnetic field for detection by the wearable device 20 to active the wearable device 20.

In general, NFC enables short range communication between compatible devices. This requires at least one transmitting device (the gateway, called NFC transmitter 10 herein) and another device to receive the signal (the wearable device 20, e.g. in the form of a wearable patch). Known wearable devices have a passive NFC tag and other small transmitters that can send information to other NFC devices (i.e. device that have NFC functionality for transmitting and/or receiving signals via NFC) without the need for a power source of their own. This means that passive devices do generally not require their own power supply, but can instead be powered by the electromagnetic field produced by an active NFC component when it comes into range. This is also exploited according to the present invention.

The NFC transmitter 10 is, in this embodiment, included in a portable device 11, such as a smartphone or tablet, but may also be configured as a separate, standalone entity. It comprises NFC circuitry 12, including in particular an NFC controller, a card (e.g. SIM) emulator and transmission circuitry, and a transmitter antenna 13 for transmission of data 30 and energy 31 and for reception of data 30 via NFC 32.

The wireless device 20 comprises an electronic circuit 21, e.g. a processor that seeks to perform a predetermined function (for instance, measuring and/or processing of sensor signals such as vital signs of a patient). The wireless device 20 further comprises a power supply 22, such as a battery, which is coupled to the electronic circuit 21 via a switching circuit 23 coupled between the electronic circuit 21 and the power supply 22.

An electromagnetic field detection circuit 24 is coupled to the switching circuit 23 via connection line 25 for detecting an electromagnetic field generated by the NFC transmitter 10 within the detection range (e.g. up to a few centimeters, such as 20 cm at maximum, but usually less than 5 cm) of the electromagnetic field detection circuit 24. The electromagnetic field detection circuit 24 generates a trigger signal if an electromagnetic field generated by an NFC transmitter 10 is detected within the detection range of the electromagnetic field detection circuit 24. The electromagnetic field detection circuit 24 may e.g. comprise a device antenna 241 and an NFC tag 242.

In the embodiment shown in FIG. 1 the switching circuit 23 comprises a flip-flop 231 to switch the connection 28 between the electronic circuit 21 and the power supply 22 on and off (depending on the current state) in response to the trigger signal. Hence, the NFC tag 242 will trigger the flip-flop 231 which is fed by the power supply 22 via feeding line 26. The flip-flop 231 can activate a switching transistor 232, which is coupled via gate line 27 to the flip-flop 231. In this way, the wireless device 20 will be powered up. In the same manner the wireless device 20 can also be deactivated to save battery power. In this way the user has complete control of the wireless device 20, which provides a significant advantage compared to the known solutions.

The switching transistor 232 may be implemented by a FET, wherein the gate 233 of the switching transistor 232 is connected to the output of the flip-flop 231, the source 234 of the switching transistor 232 is connected to the power supply 22 and the drain 235 of the switching transistor 232 is connected to the electronic circuit 21.

From a perspective of the wearable device 20 the NFC communication and the pairing goes passively. One idea of the present invention is to use the energy transmitted by the NFC transmitter 10 to trigger an electronic switch to power the wireless device 20. Hence, the wireless device 20 does not need to be in a deep sleep or standby mode (which consumes power), but can be completely switched on in a passive way. In this way the costs and surface of a physical switch can be saved and the wireless device 20 has a maximum shelf time, which is only determined by the self-discharge of the power supply 22. Furthermore, the wireless device 20 can be completely enclosed in an air- and/or water-tight cover or casing 29 to increase the air- and/or water-resistivity.

To provide reliable pairing the NFC transmitter 10 may additionally include the ID of the wireless device 20 or of the NFC tag 21. Hence, only the identified wireless device 20 will be powered, while all other wireless devices will not be powered so that incorrect pairing is efficiently avoided. Further, the NFC transmitter 10 may sends a command to the wireless device 20 to trigger the electronic switch to power the wireless device 20.

FIG. 2 shows a schematic diagram of a second embodiment of a system 2 and wearable device 40 according to the present invention. In this embodiment the switching circuit 43 of the wireless device 40 comprises a transistor circuit 431 including an input transistor 432 and a fuse 433 to switch the connection 28 between the electronic circuit 21 and the power supply 22 on in response to the trigger signal from the electromagnetic field detection circuit 24.

In an embodiment the input transistor 432 may also be implemented by a FET, wherein the gate 434 and the source 435 of the input transistor 432 are connected to the electromagnetic field detection circuit 24. Further, the fuse 433 is coupled between the drain 436 of the input transistor 432 and ground 437.

Further, in this embodiment the gate 233 of the switching transistor 232 is connected to the terminal of the fuse 433, which is connected to the drain 436 of the input transistor 432. A resistor 438, e.g. a pull up mega-ohm resistor, may be coupled between the power supply 22 and the gate 233 of the switching transistor 232.

The fuse 433, e.g. a low power fuse, is particularly configured to melt in response to detection of the electromagnetic field generated by the NFC transmitter 10, i.e. the generated power is used to melt the fuse 433. Hence, once presence of the NFC transmitter 10 has been detected and, optionally, its request has passed an identifier check, the input transistor 432 will switch on. This sequence will be powered by applied external NFC field. Besides this, the NFC field is also be used to melt the fuse 433, optionally after a valid identifier check. After the fuse 433 is melted, the connection between the ground 437 and the drain 436 is interrupted. Consequently, the input transistor 432 will activate the switching transistor 232, which is coupled via gate line 233 to the drain 436 of the input transistor 432. This will trigger the switching circuit 43, and the switching transistor 232 will be activated to connect the power supply 22 with the electronic circuit 21. In contrast to first embodiment of the wireless device 20 shown in FIG. 1, the wireless device 40 cannot be switched off by a transmitter command, but will be switched on permanently due to the melting of the fuse 433.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A wearable device comprising:
   an electronic circuit,
   a power supply,
   a switching circuit coupled between the electronic circuit and the power supply, and
   an electromagnetic field detection circuit coupled to the switching circuit for detecting an electromagnetic field generated by a Near Field Communication (NFC) transmitter within a detection range of the electromagnetic field detection circuit and for generating a trigger signal if the electromagnetic field generated by the NFC transmitter is detected within the detection range of the electromagnetic field detection circuit,
   wherein the switching circuit comprises a switching transistor to switch the electrical circuit on, an electrical ground, and a transistor circuit, the transistor circuit including an input transistor and a fuse connected to the input transistor, the switching transistor, and the electrical ground, to connect the electronic circuit and the power supply, via the switching transistor, in response to the trigger signal,
   wherein the fuse is configured to melt, interrupting a connection between the input transistor and the electrical ground, in response to detection of the electromagnetic field generated by the NFC transmitter to allow the input transistor to activate the switching transistor to connect the electronic circuit with the power supply in response to the trigger signal.

2. The wearable device according to claim 1,
wherein the switching circuit comprises a switching transistor;
wherein a gate of the switching transistor is connected to the output of the transistor circuit, a source of the switching transistor is connected to the power supply and a drain of the switching transistor is connected to the electronic circuit.

3. The wearable device according to claim 1,
wherein a gate of the switching transistor and the source of the input transistor are connected to the electromagnetic field detection circuit.

4. The wearable device according to claim 3,
wherein the fuse is coupled between a drain of the input transistor and ground.

5. The wearable device according to claim 4,
wherein the gate of the switching transistor is connected to a terminal of the fuse, which is connected to the drain of the input transistor.

6. The wearable device according to claim 5,
wherein a resistor is coupled between the power supply and the gate of the switching transistor.

7. The wearable device according to claim 1,
wherein the electromagnetic field detection circuit is configured to generate a trigger signal in response to a command from the NFC transmitter or in response to reception of an identifier identifying at least one of the device or the NFC transmitter.

8. The wearable device according to claim 1,
wherein the electromagnetic field detection circuit comprises an NFC tag and a device antenna.

9. The wearable device according to claim 8, wherein the device antenna is a loop antenna or coil.

10. The wearable device according to claim 1,
further comprising at least one of a watertight cover and an airtight cover.

11. A system comprising:
a wearable device comprising:
an electronic circuit;
a power supply;
a switching circuit coupled between the electronic circuit and the power supply; and
an electromagnetic field detection circuit coupled to the switching circuit for detecting an electromagnetic field generated by a Near Field Communication (NFC) transmitter within a detection range of the electromagnetic field detection circuit and for generating a trigger signal if the electromagnetic field generated by the NFC transmitter is detected within the detection range of the electromagnetic field detection circuit;
wherein the switching circuit comprises a switching transistor to switch the electrical circuit on, an electrical ground, and a transistor circuit, the transistor circuit including an input transistor and a fuse connected to the input transistor, the switching transistor, and the electrical ground, to connect the electronic circuit and the power supply, via the switching transistor, in response to the trigger signal; and
wherein the fuse-is configured to melt, interrupting a connection between the input transistor and the electrical ground, in response to detection of the electromagnetic field generated by the NFC transmitter to allow the input transistor to activate the switching transistor to connect the electronic circuit with the power supply in response to the trigger signal.

12. The system as claimed in claim 11,
wherein the wearable device is a medical wearable device, and wherein the NFC transmitter is configured as or included in a portable device.

13. The system as claimed in claim 12, wherein the medical wearable device is a patch for mounting at a subject.

* * * * *